(12) United States Patent
Stolpe et al.

(10) Patent No.: US 10,004,947 B2
(45) Date of Patent: Jun. 26, 2018

(54) DETECTION METHOD FOR VOLLEY-BALL FUNCTION

(71) Applicant: Swatch AG, Bienne (CH)

(72) Inventors: Alexander Stolpe, Leipzig (DE); Markus Streicher, Leipzig (DE); Adib Taraben, Leipzig (DE); Christoph Eckelmann, Leipzig (DE)

(73) Assignee: Swatch AG, Bienne (CH)

( * ) Notice: Subject to any disclaimer, the term of this patent is extended or adjusted under 35 U.S.C. 154(b) by 5 days.

(21) Appl. No.: 15/217,197

(22) Filed: Jul. 22, 2016

(65) Prior Publication Data
US 2017/0028259 A1 Feb. 2, 2017

(30) Foreign Application Priority Data

Jul. 28, 2015 (EP) .................................... 15178664

(51) Int. Cl.
*A63F 9/24* (2006.01)
*A63B 24/00* (2006.01)
*A61B 5/00* (2006.01)
*A61B 5/11* (2006.01)
*G06K 9/00* (2006.01)

(52) U.S. Cl.
CPC ............ *A63B 24/0062* (2013.01); *A61B 5/11* (2013.01); *A61B 5/681* (2013.01); *A61B 5/725* (2013.01); *A61B 5/7264* (2013.01); *G06K 9/00536* (2013.01); *A61B 2503/10* (2013.01); *A61B 2560/0209* (2013.01); *A61B 2562/0219* (2013.01); *A63B 2024/0071* (2013.01); *A63B 2220/40* (2013.01); *A63B 2243/0095* (2013.01); *G06K 9/00342* (2013.01)

(58) Field of Classification Search
None
See application file for complete search history.

(56) References Cited

U.S. PATENT DOCUMENTS

| | | | |
|---|---|---|---|
| 6,522,266 B1 | 2/2003 | Soehren et al. | |
| 2011/0196262 A1 | 8/2011 | McLeod et al. | |
| 2014/0275854 A1* | 9/2014 | Venkatraman ......... | A61B 5/721 600/301 |
| 2014/0276119 A1 | 9/2014 | Venkatraman et al. | |
| 2014/0288436 A1 | 9/2014 | Venkatraman et al. | |
| 2014/0288438 A1 | 9/2014 | Venkatraman et al. | |
| 2015/0133206 A1* | 5/2015 | Sarrafzadeh .......................... | 3/235 |
| 2015/0196256 A1 | 7/2015 | Venkatraman et al. | |

OTHER PUBLICATIONS

European Search Report dated Feb. 9, 2016 in European Application 15178664, filed on Jul. 28, 2015 ( with Written Opinion).

* cited by examiner

*Primary Examiner* — Paul A D'Agostino
(74) *Attorney, Agent, or Firm* — Oblon, McClelland, Maier & Neustadt, L.L.P.

(57) ABSTRACT

The present invention concerns a method of detection for an electronic apparatus comprising a case containing an electronic module powered with electrical energy by a means of storing electrical energy, said electronic module including a calculation unit connected to an accelerator sensor and to a memory unit, said electronic module also being connected to a display means so as to display information linked to some data of said accelerator sensor.

9 Claims, 2 Drawing Sheets

DETECTION METHOD FOR VOLLEY-BALL FUNCTION

This application claims priority from European Patent Application No 15178664.7 filed Jul. 28, 2015, the entire disclosure of which is hereby incorporated herein by reference.

The present invention concerns a method of detection for an electronic apparatus comprising a case containing an electronic module powered with electrical energy by a means of storing electrical energy, said electronic module including a calculation unit connected to an accelerator sensor and to a memory unit, said electronic module also being connected to a display means so as to display information linked to some data of said accelerator sensor

BACKGROUND OF THE ART

A portable electronic object, such as an electronic device or, for example, a portable timepiece, includes a case generally formed of a middle part closed by a back cover and by a glass. Inside the case is arranged an electronic module so as to provide an information. This information could be an information linked to an activity. These activities are mainly linked to fitness like running or walking.

To do this, the electronic module includes at least one sensor like an accelerator sensor. This electronic circuit also included a calculation unit so as to use data coming from the accelerator sensor and a memory to save them.

In the calculation unit, an algorithm is implemented. Said algorithm is programmed to treat said data so as to obtain data representative of an activity.

However, currently, it is difficult to have an algorithm which is able to precisely determine the activity. For example, for pedometer, it is quite difficult for the calculation unit and the algorithm to determine if the user walks or runs. Yet, the determination of a walking activity or a running activity is important to calculate the crossed distance.

Consequently, if it is difficult to determine the action for simple activity like running or walking, it is more difficult to provide a portable object for detected complex actions like volleyball.

Indeed, in volleyball, there are different categories of volleyball techniques that can be differentiated. In addition to that, the force of the impact on the ball is determined, named "smash power" hereinafter.

SUMMARY OF THE INVENTION

The object of the present invention is to provide an algorithm, used for example in a volleyball activity, able to detect and characterize ball contacts in a beach volleyball game like serves, passes, digs etc.

The invention therefore concerns a method for managing an electronic apparatus comprising a case containing an electronic module powered with electrical energy by a means of storing electrical energy, said electronic module including a calculation unit connected to an accelerator sensor and to a memory unit, said electronic module also being connected to a display means so as to display information linked to some data of said accelerator sensor, the method including the steps of:

Acquiring data from the accelerator sensor;
Detecting potential activities using a high-pass filter the acquired data so as to detect fast changes of the measured acceleration and using a low pass filter to filter the norm of the high-passed filtered data to only detect significant activities;
Filtering the maxima of the low-pass filtered high pass norm above a second threshold to reject more of the non-relevant activities;
Preparing the data for the classification wherein acceleration data before and after the peak/hit is low-pass filtered from both ends towards the hit and down-sampled, starting with the value closest to the hit, and wherein the down-sampled data is handed over the classification step of the algorithm that tries to determine what activity occurred;
Characterizing the technique wherein the characterization is based on a 1-Nearest Neighbor algorithm using the L1-norm.

In a first advantageous embodiment, it further includes a step of determining the hit power consisting in using a band-pass filter to filter acceleration data in a certain window before and after the hit, the sum over the norm of the band-passed filtered data being correlated with the speed of the ball.

In a second advantageous embodiment, the calculation unit is able to pass from a low power mode wherein said calculation unit sleeps to a normal mode wherein said calculation unit wakes up if the accelerator sensor which constantly acquires data with approximately an appropriate frequency, measures an acceleration data above a determined threshold.

In a third advantageous embodiment, the low-pass filter and the high-pass filter use an infinite-impulse response filter of second order.

BRIEF DESCRIPTION OF THE DRAWINGS

The objects, advantages and features of the portable electronic device or object according to the present invention will appear more clearly in the following detailed description of at least one embodiment of the invention, given solely by way of non-limiting example and illustrated by the annexed drawings, in which.

DETAILED DESCRIPTION

The portable object according to the present invention is a wristwatch comprised in a case. Said case forms a housing wherein an electronic circuit is placed. Said electronic circuit comprises a calculation unit or processing unit for managing the electronic circuit, a sensor for acquiring data and a memory so as to save these data. The portable object also comprises display means like LCD display so as to display the data.

This portable object could be used during sport activity like volleyball. In volleyball, there are numerous different categories of volleyball techniques that can be differentiated like a dig, a dig with a jump, a lower pass, a high pass, an attack, a jump attack and so on. In addition to that, the force of the impact on the ball is determined, named "smash power" hereinafter. Common to the volleyball techniques is that the ball normally hits the lower arm in close proximity to the wrist. This gives the possibility to acquire acceleration sensor data with a watch on the wrist to determine and characterize the used techniques.

The sensor is a 3D acceleration sensor with a measurement range between −16 g and +16 g is attached to the wrist in such a way that the sensor axes are aligned with the lower arm. Pointing along the lower arm bone, perpendicular to the palm of the hand and horizontally when the arm is pointing downwards. For example, this is useful since many of the arm movements during a volleyball game are causing distinct accelerations along these axes. The acceleration sensor is set to acquire data with a frequency comprised between 30 Hz and 50 Hz, preferably between 35 Hz and 45 Hz, most preferred about 40 Hz in the low power mode.

Figure 1:
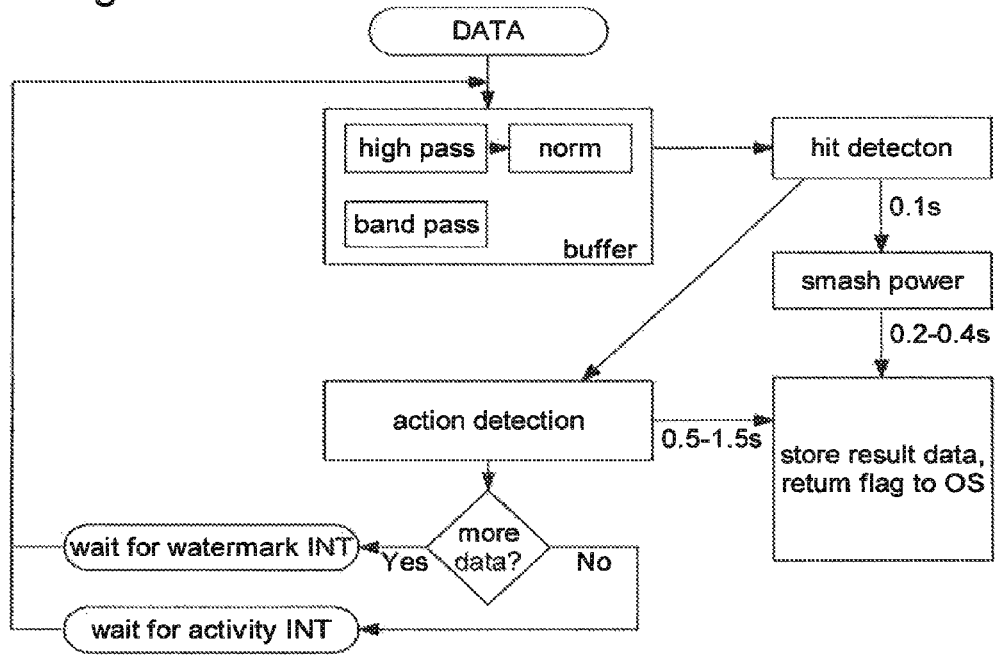
FIGS. 1 and 2 are schematic diagram of the managing method according to the invention.
Figure 2:
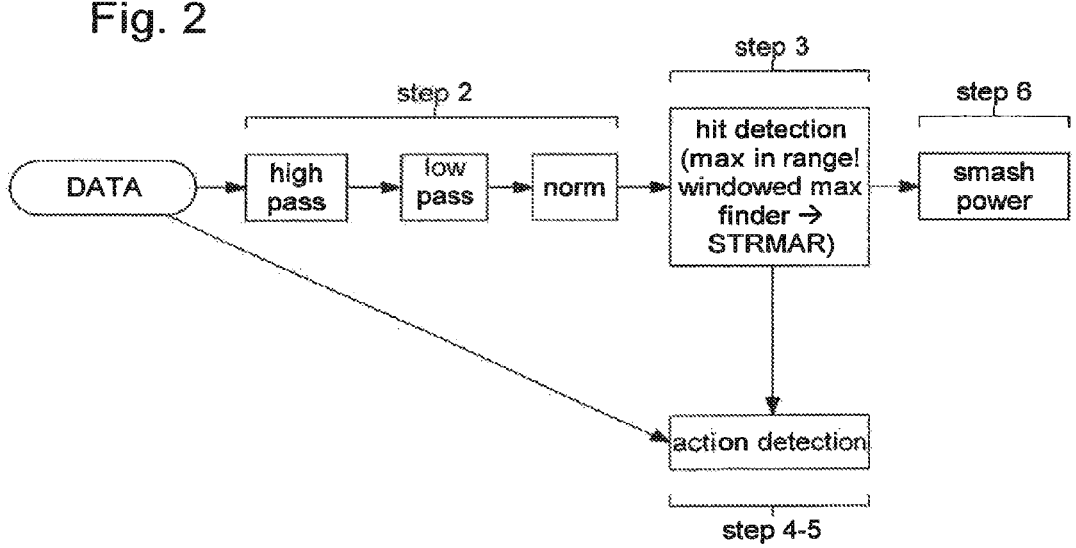

The calculation unit of the portable object further includes an algorithm able to treat said acceleration data so as to obtain data representative of an activity. For the present description, the activity is volleyball. The volleyball action detection algorithm is based on a multi-layer approach as seen in FIGS. 1 and 2. An activity is defined by a change in acceleration data above a certain threshold. In the watch, it is used an activity interrupt in such a way that only when the acceleration sensor detects an activity, the operating system is notified and the acceleration data is retrieved. If the sensor does not detect an activity and therefore does not send an activity interrupt to the operating system, the operating system would never retrieve the acceleration data and therefore never start the algorithm.

In the first step of the detection algorithm, the acceleration sensor is set to a threshold-interrupt mode, constantly acquiring data in the low power mode with approximately 40 Hz, storing it in a ring-buffer and checking whether an acceleration above a determined threshold is measured. This threshold should be comprised between 1 g and 3 g, preferably between 1.5 g and 2.5 g and most preferred about 2 g. In case an acceleration above the threshold is measured, the microcontroller on which the algorithm is running wakes up and the ring-buffered acceleration data is transferred to the microcontroller. To explain more precisely, the acceleration sensor acquires data with a certain rate. In the present case 40 Hz. The acceleration data is then first stored in the acceleration sensor itself until the operating system retrieves the acceleration data in chunks. By setting a watermark interrupt, the operating system tells the acceleration sensor how many datasets the acceleration sensor should store until it notifies the Operating system. In our case, the watermark was set to 20. That means, each time the acceleration sensor stored a number of 20 datasets it notifies the operating system. The operating system then retrieves the acceleration data from the sensor thereby moving the data out of the storage of the sensor into the operating system. The acceleration sensor then fills up its own storage again with new acceleration data and again notifies the operating system once it reaches 20 acceleration datasets in storage. The limit of in our case 20 is called the watermark level. Each time the watermark level is reached the acceleration sensor sends a system interrupt to the operating system. Causing the operating system to retrieve the sensor data.

The second step of the detection algorithm is to detect potential volleyball activities. To do this, the acceleration data is high-pass filtered with an efficient infinite-impulse response (IIR) filter of second order. The cut-off frequency should be comprised between 5 Hz and 15 Hz, preferably between 7 Hz and 13 Hz and most preferred about 9 Hz. This is done to detect fast changes of the measured acceleration.

To only detect significant activities, i.e. ball contact with the arm, the norm (squared sum of the x-y-z axis) of the high-passed filtered data is calculated and low pass filtered (again with an IIR filter of second order). The cut-off frequency should be comprised between 1 Hz and 10 Hz, preferably between 2 Hz and 6 Hz and most preferred about 3 Hz.

Likely times for a volleyball technique might be peaks of this norm above a second threshold. This second threshold should be comprised between 0.1 g and 1 g, preferably between 0.2 g and 0.6 g, most preferred about 0.3 g. At this stage the detected maxima were approximately 55% to 70% non-relevant activities and 30% to 45% volleyball activities of interest. The response delay of the IIR filters with respect to the raw acceleration data is taken into account for all the following operations.

In a third step, maxima of the low-pass filtered high pass norm above the second threshold are further analyzed in another filter to reject more of the non-relevant activities.

Data analysis showed that most of the non-relevant maxima of the filter described in the second step had a relatively low value of the high-passed maxima and a low value for the norm of the raw acceleration data just before the peak (between 5 and 10 raw accelerations values before the peak were averaged), while most of the relevant volleyball activities are characterized either by a high peak in the high-passed data or a high value of the raw acceleration data or both.

This filter is implemented by separating the 2D space (high-pass norm peak value and raw acceleration norm before the peak) by a line with peaks above the line being further processed and peaks below (relatively low high-pass peak and low raw acceleration norm) the line are sorted out. This reduces the ratio of non-relevant to relevant volleyball activities (ball contact, i.e. hit) to approximately 1:1. There are about 25 to 35 (for each acceleration sensor axis) raw acceleration measurements before and 15 to 25 after the high-pass peak (i.e. likely ball contact) are then transferred to the next function.

In the fourth step of the algorithm, the data is prepared for the classification. The 3D raw acceleration data before and after the peak/hit (not including the acceleration data at the peak) is low-pass filtered from both ends towards the hit, this means that, in a data interval centered on the peak, the filtering is operated from the data at the ends of the interval to the data towards said peak. The 3D raw acceleration data are also down-sampled by a factor between 2 and 4, starting with the value closest to the hit (from the hit towards the ends). The low-pass filter could be the same IIR filter as the filter disclosed and used in the second step.

The down-sampled data is then handed over the classification step of an algorithm that tries to determine what kind of activity and preferentially volleyball activity occurred (also sorting out non-relevant activities).

Figure 3:
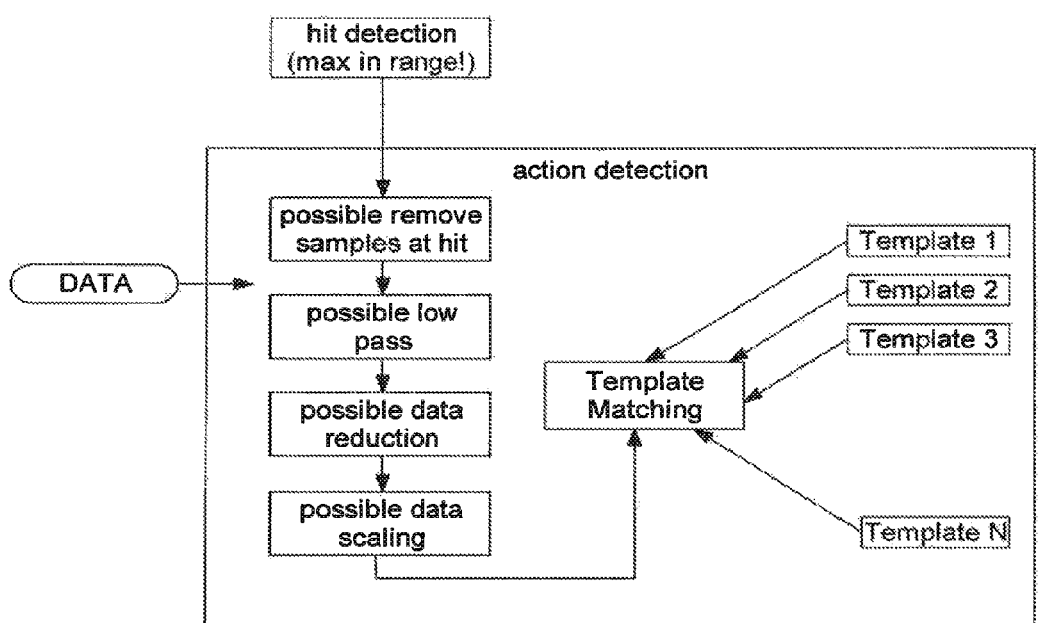
FIG. 3 is a schematic diagram of a characterizing step according to the invention.

In a fifth step, volleyball technique characterization is done as seen in FIG. 3. Said volleyball technique characterization is based on a 1-Nearest Neighbor algorithm using the L1-norm in the downsampled acceleration data space. The L1-norm is calculated to cluster centers each uniquely related to a volleyball technique (i.e. jump attack, serve low, . . . ) or several other common activities which occur during a normal volleyball game (i.e. clapping, checks with on another) or fan activities like clapping or Ia OIa. Each volleyball technique is linked to a memory location. Thus, each time the volleyball technique occurs, the number in the memory location is increased. So, at the end, it is possible to display the number of occurrence for each volleyball technique with a timestamp of when it occurred In an alternative embodiment, the method according to the present invention also includes a sixth step. In this sixth step, the smash power, that correlates with the ball speed, is determined. The smash power is determined in the following way: When a volleyball technique was detected the raw acceleration data in a certain window of about 0.6 s to 0.8 s before and after the hit is band passed with an IIR filter of second order. The sum over the norm of the band-passed filtered data highly correlates with the speed of the ball. Since the watch only reserved 2 digits to display the integrated smash power the sum over the band-pass filtered data is scaled to a range from 0 to 99. Multiplying the smash power with another factor, it is possible to determine a ball speed that highly correlates with the actual ball speed.

Said power is affiliated to a volleyball technique. Said power is also saved in the memory. The memory could be managed so that for each detected volleyball activity, the power of said detected activity is saved. It must be understood that for each smash or each pass or each serve, the power is saved. The portable object is thus able to display, for each occurrence, the power of the volleyball activity.

Each time a volleyball activity is detected and saved by the volleyball algorithm the operating system of the watch is notified. In this way the watch can update the display.

It will be clear that various alterations and/or improvements and/or combinations evident to those skilled in the art may be made to the various embodiments of the invention set out above without departing from the scope of the invention defined by the annexed claims.

It will be understood that this method could be used for others activities like basketball or baseball or tennis or badminton. Moreover, it will be understood that this method could be used to differentiate a clap of a player from a hit or a serve. Consequently, the efficiency of the portable object including said method is higher. It is also possible to have a specific function in the portable object concerning clapping or Ia oIa.

What is claimed is:

1. A method of detection for an electronic apparatus comprising a case containing an electronic module powered with electrical energy by an electrical energy storage, said electronic module including processing circuitry connected to an acceleration sensor and to a memory, said electronic module also being connected to a display so as to display information linked to at least some data of said accelerator sensor, the method comprising:
   acquiring data from the accelerator sensor;
   detecting one or more potential activities of a wearer of the electronic apparatus using a high-pass filter to filter the acquired data so as to detect fast changes of a measured acceleration and using a low pass filter to filter a calculated norm of the high-passed filtered data to only detect one or more significant activities in which there is a hit of an object with the wearer of the electronic apparatus;
   filtering maxima of the low-pass filtered high pass norm above a second threshold to reject more of non-relevant activities and to determine peak/hit of this norm;
   preparing the data for a classification wherein acceleration data before and after the peak/hit is low-pass filtered from both ends towards the hit and down-sampled, starting with a value closest to the hit, and wherein the down-sampled data is handed over to the classification of an algorithm that tries to determine what activity occurred in the hit of the object with the wearer of the electronic apparatus; and
   determining from the down-sampled data, with the processing circuitry, what activity occurred in the hit of the object with the wearer of the electronic apparatus by a characterization of the one or more significant activities without the rejected non-relevant activities based on a 1-Nearest Neighbor algorithm using an L1-norm in a down sampled acceleration space.

2. The method according to claim 1, further comprising determining a hit power of the hit including using a band-pass filter to filter acceleration data in a certain window before and after the hit, a sum over a norm of the band-passed filtered data being correlated with a speed of a ball.

3. The method according to claim 1, wherein the processing circuitry is to pass from a low power mode wherein said processing circuitry sleeps to a normal mode wherein said processing circuitry wakes up when the accelerator sensor, which constantly acquires data with approximately between 30 to 50 Hz Hz, measures an acceleration data above a determined threshold.

4. The method according to claim 3, wherein the determined threshold is comprised between 1.5 and 2.5 g.

5. The method according to claim 1, wherein the low-pass filter and the high-pass filter use a filter of second order.

6. The method according to claim 1, wherein the second threshold is comprised between 0.2 and 0.6 g.

7. The method according to claim 1, wherein the electronic apparatus is a portable object.

8. The method according to claim 1, wherein the electronic apparatus is a wristwatch.

9. The method according to claim 1, wherein the hit of the object with the wearer of the electronic apparatus is a contact of a ball with the wearer of the electronic apparatus.

* * * * *